United States Patent
Cornet et al.

(10) Patent No.: US 9,381,284 B2
(45) Date of Patent: Jul. 5, 2016

(54) SYSTEM AND METHOD FOR SEALING AN INCISIONAL WOUND

(71) Applicant: KCI Licensing, Inc., San Antonio, TX (US)

(72) Inventors: Douglas A. Cornet, Barboursville, VA (US); Michael E. Manwaring, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 260 days.

(21) Appl. No.: 14/088,027

(22) Filed: Nov. 22, 2013

(65) Prior Publication Data

US 2014/0081227 A1    Mar. 20, 2014

Related U.S. Application Data

(62) Division of application No. 13/095,384, filed on Apr. 27, 2011, now Pat. No. 8,623,047.

(60) Provisional application No. 61/329,764, filed on Apr. 30, 2010.

(51) Int. Cl.
*A61B 17/08* (2006.01)
*A61M 27/00* (2006.01)
(Continued)

(52) U.S. Cl.
CPC ............ *A61M 1/0088* (2013.01); *A61B 17/085* (2013.01); *A61F 13/00068* (2013.01);
(Continued)

(58) Field of Classification Search
CPC ........... A61M 1/0088; A61F 13/00068; A61F 2013/00221; A61F 2013/00455; A61F 2013/00536; A61F 2013/0054; A61B 17/085; A61B 2017/00893; A61B 2019/465; A61B 2017/306

See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 A1    3/1986
AU    745271    4/1999
(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
(Continued)

*Primary Examiner* — Julian W Woo

(57) ABSTRACT

An apparatus, system, and method for treating an incisional wound having incisional walls is disclosed. The apparatus includes a conduit having a first end for receiving reduced pressure and a second end. The apparatus further includes a scaffold. The scaffold has opposing surfaces for positioning adjacent the incisional walls and is fluidly coupled to the second end of the conduit for receiving the reduced pressure. The scaffold is generally elongated in shape and has a thickness between the opposing surfaces that is sufficiently thin for positioning within the incisional wound. The apparatus further includes an internal manifold that has a primary flow channel extending generally longitudinally within the scaffold and between the opposing surfaces of the scaffold. The internal manifold is fluidly coupled to the second end of the conduit. The application of the reduced pressure through the scaffold and the internal manifold induces tissue apposition between the incisional walls.

16 Claims, 4 Drawing Sheets

(51) Int. Cl.
 *A61M 1/00* (2006.01)
 *A61F 13/00* (2006.01)
 *A61B 17/00* (2006.01)
 *A61B 17/30* (2006.01)

(52) U.S. Cl.
 CPC . *A61B2017/00893* (2013.01); *A61B 2017/306* (2013.01); *A61F 2013/0054* (2013.01); *A61F 2013/00221* (2013.01); *A61F 2013/00455* (2013.01); *A61F 2013/00536* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,381,211 B2 * | 6/2008 | Zamierowski | A61B 17/064 606/216 |
| 8,267,918 B2 * | 9/2012 | Johnson | A61B 17/88 604/23 |
| 8,715,267 B2 | 5/2014 | Bengtson et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0039415 A1 | 2/2004 | Zamierowski | |
| 2006/0079852 A1 | 4/2006 | Bubb et al. | |
| 2007/0185426 A1 * | 8/2007 | Ambrosio | A61F 13/0216 602/43 |
| 2007/0219497 A1 | 9/2007 | Johnson et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/01173 A1 | 1/1999 |

(56) References Cited

FOREIGN PATENT DOCUMENTS

| WO | 99/13793 | 3/1999 |
|---|---|---|
| WO | 2007/041642 A2 | 4/2007 |
| WO | 2007/106591 A2 | 9/2007 |
| WO | 2009/049232 A1 | 4/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ ukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

SYSTEM AND METHOD FOR SEALING AN INCISIONAL WOUND

CROSS-REFERENCE TO RELATED APPLICATIONS

This application is a divisional of U.S. patent application Ser. No. 13/095,384, filed on Apr. 27, 2011, now U.S. Pat. No. 8,623,047, which claims the benefit of U.S. Provisional Application No. 61/329,764, filed Apr. 30, 2010. Each of the above applications are incorporated herein by reference.

BACKGROUND OF THE INVENTION

1. Field of the Invention

The present disclosure relates generally to medical treatment systems and in particular to apparatuses and systems suitable for use as scaffolds in the treatment of wounds.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Synthetic and biologic scaffolds have been utilized to provide three-dimensional frameworks for augmenting endogenous cell attachment, migration, and colonization. To date, nearly all scaffolds have been designed with the idea that they can be made to work with the biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process. Taken together, these complications can all lead to less than desired functional tissue regeneration at the injury site.

It would therefore be advantageous to provide additional systems and apparatuses for the repair or regeneration of tissues resulting from specific injuries or incisions at various tissue sites. The present invention provides such systems and apparatuses.

SUMMARY

The systems, apparatuses, and methods of the illustrative embodiments described herein include an apparatus for treating an incisional wound having incisional walls. The apparatus includes a conduit having a first end for receiving reduced pressure and a second end. The apparatus further includes a scaffold. The scaffold has opposing surfaces for positioning adjacent the incisional walls and is fluidly coupled to the second end of the conduit for receiving the reduced pressure. The scaffold is generally elongated in shape and has a thickness between the opposing surfaces that is sufficiently thin for positioning within the incisional wound. The apparatus further includes an internal manifold that has a primary flow channel extending generally longitudinally within the scaffold and between the opposing surfaces of the scaffold. The internal manifold is fluidly coupled to the second end of the conduit. The application of the reduced pressure through the scaffold and the internal manifold induces tissue apposition between the incisional walls.

According to another illustrative embodiment, a system for treating an incisional wound having incisional walls includes a pressure source to supply reduced pressure, a conduit fluidly coupled to the pressure source that has a first end for receiving the reduced pressure and a second end, and a scaffold fluidly coupled to the second end of the conduit. The scaffold has opposing surfaces, is formed from a porous material, and is generally elongated in shape. The system further includes an internal manifold that has a primary flow channel extending generally longitudinally within the scaffold between the opposing surfaces. The internal manifold is fluidly coupled to the second end of the conduit. The application of the reduced pressure through the scaffold and the internal manifold induces tissue apposition between the incisional walls.

According to another illustrative embodiment, a system for treating an incisional wound having incisional walls includes a pressure source to supply reduced pressure, a conduit fluidly coupled to the pressure source that has a first end for receiving the reduced pressure and a second end, and a scaffold fluidly coupled to the second end of the conduit. The scaffold has opposing surfaces, is formed from a porous material, and is generally elongated in shape. The system further includes an internal manifold that has a primary flow channel extending generally longitudinally within the scaffold between the opposing surfaces. The internal manifold is fluidly coupled to the second end of the conduit. The internal manifold further includes tributary flow channels fluidly coupled to the primary flow channel and extending generally transversely within the scaffold between the opposing surfaces. The tributary flow channels extend generally perpendicular from the primary flow channel. The application of the reduced pressure through the scaffold and the internal manifold induces tissue apposition between the incisional walls.

According to yet another illustrative embodiment, a method for treating an incisional wound having incisional walls includes fluidly coupling a conduit to a source of reduced pressure, wherein the conduit has a first end for receiving reduced pressure and a second end. The scaffold is fluidly coupled to the second end of the conduit for receiving the reduced pressure, wherein the scaffold is formed from sufficiently thin porous material having an internal manifold extending generally longitudinally between opposing surfaces of the scaffold. The opposing surfaces of the scaffold are positioned between the incisional walls of the incisional wound and the internal manifold is fluidly coupled to the second end of the conduit. The incisional wound is surgically closed and reduced pressure is provided through the conduit to the scaffold and the internal manifold onto the incisional wound, whereby the scaffold induces tissue apposition between the incisional walls.

Other objects, features, and advantages of the illustrative embodiments will become apparent with reference to the drawings and detailed description that follows.

DETAILED DESCRIPTION

In the following detailed description of the illustrative embodiments, reference is made to the accompanying drawings that form a part herein. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
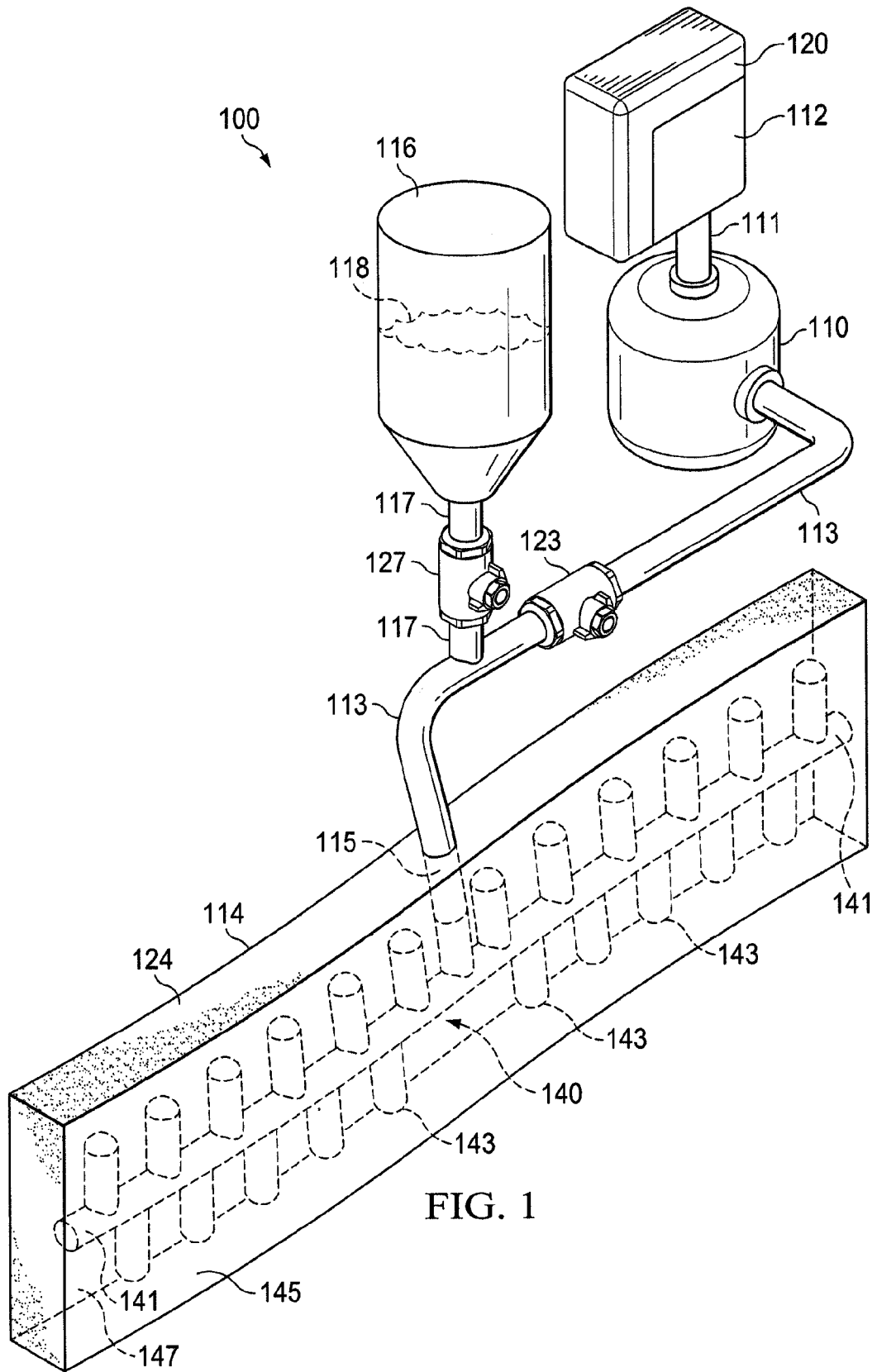
FIG. 1 is a schematic, perspective view of a reduced pressure treatment system including a scaffold according to one illustrative embodiment.
Figure 2:
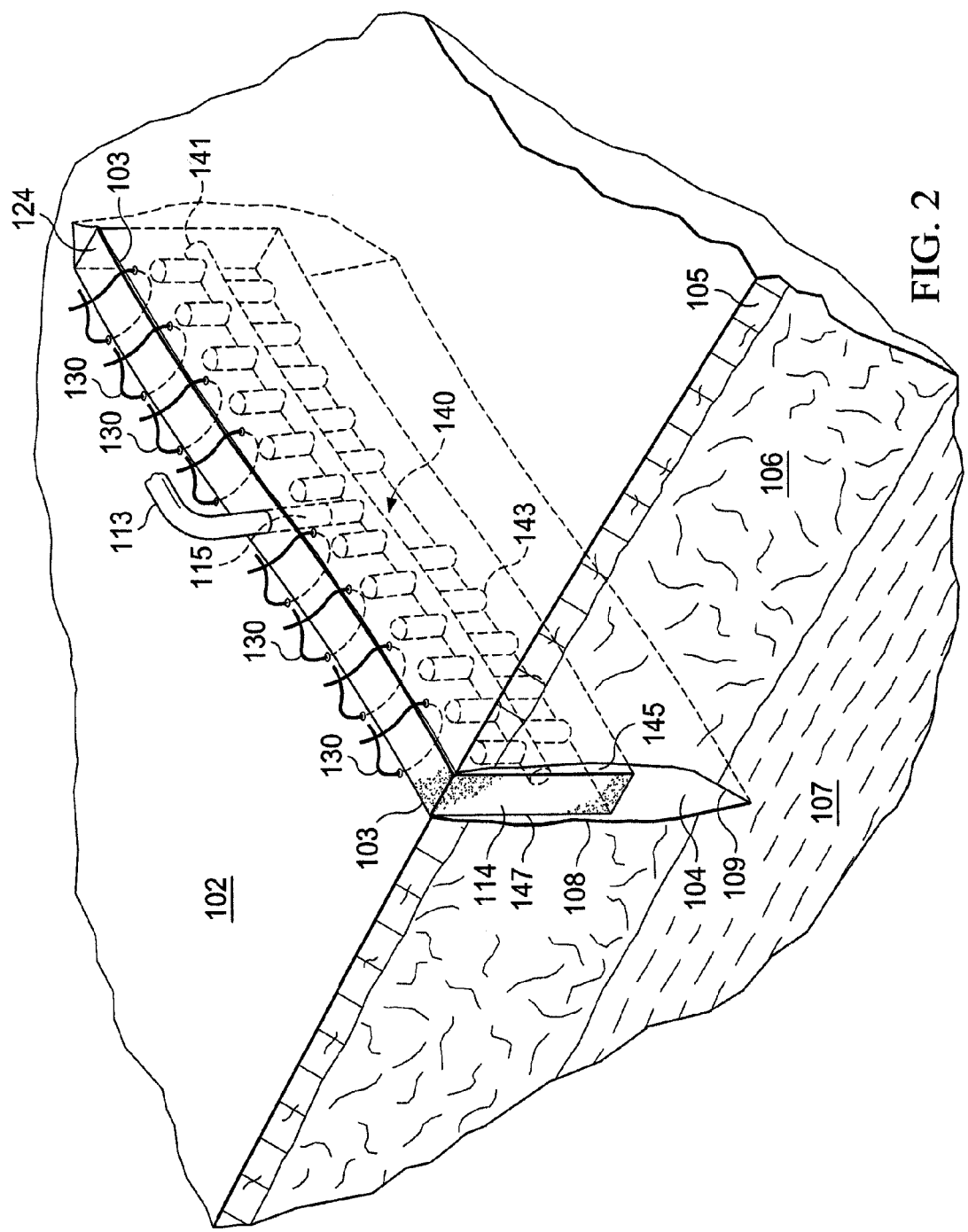
FIG. 2 is a schematic, cross-sectional, perspective view of an incisional wound and the scaffold shown in FIG. 1 positioned within the incisional wound.

Referring to FIGS. 1 and 2, a reduced pressure treatment system 100 for applying a reduced pressure to a tissue site 102 of a patient according to an illustrative embodiment is shown. The reduced pressure treatment system 100 applies reduced pressure to an incisional wound 104 through an incisional opening 103 in epidermis 105 extending through dermis 106 into the fascial layers or subcutaneous tissues 107 at the tissue site 102. The term "incisional wound" refers to severed tissue at a tissue site such as, for example, a laceration, incision, or puncture that may have been caused by trauma, surgery, or degeneration. For example, an incisional wound may be an incision or puncture made by a surgeon in otherwise healthy tissue that extends up to 40 cm or more in length. In this sense, the incisional wound 104 is substantially a long and narrow shape, elongated shape, wherein the length represents the longitudinal axis of the incisional wound 104. Incisional wounds may extend to different depths extending up to 15 cm or more, or be subcutaneous depending on the type of tissue and the cause of the incision. The depth represents the transverse axis of the incisional wound 104. The incisional wound 104 is surrounded by tissue adjacent the incisional opening 103 at the tissue site 102 and is formed by incisional walls 108 and 109. Although the incisional wound 104 is shown as an epidermal incision at the tissue site 102, the incisional wound 104 may also be, for example, an incision in an organ adjacent a fistula. Subcutaneous, absorbable sutures (not shown) may be placed in one or more fascial layers or the subcutaneous tissues 107.

The system 100 comprises a canister 110 having a filter (not shown) contained with the canister 110 and a reduced pressure source 112 coupled in fluid communication with the canister 110 via a first conduit 111. The system 100 further comprises a scaffold 114 positioned within the incisional wound 104 between the incisional walls 108, 109. The scaffold 114 includes an upper edge portion 124 positioned adjacent the incisional opening 103 of the incisional wound 104, a lower edge portion 125, and opposing, interfacial surfaces 145 and 147 positioned adjacent the faces of the incisional walls 109 and 108, respectively, of the incisional wound 104. The scaffold 114 is coupled in fluid communication with the reduced pressure source 112 through the canister 110 via a second conduit 113 which is fluidly coupled to the scaffold 114 by a conduit connector 115. The system 100 may also comprise a fluid supply 116 coupled in fluid communication to the scaffold 114 via a third conduit 117 either directly (not shown) or indirectly through the second conduit 113 for delivering a fluid 118 to the incisional wound 104 at the tissue site 102.

The reduced pressure source 112 is an electrically-driven vacuum pump. In another implementation, the reduced pressure source 112 instead may be a manually-actuated or manually-charged pump that does not require electrical power. The reduced pressure source 112 may be any other type of reduced pressure pump, or alternatively a wall suction port such as those available in hospitals and other medical facilities. The reduced pressure source 112 may be housed within or used in conjunction with a reduced pressure treatment unit 120 which may also contain a processing unit, sensors, alarm indicators, memory, databases, software, display units, and user interfaces that further facilitate the application of reduced pressure treatment to the tissue site 102. In one example, a sensor or switch (not shown) may be disposed at or near the reduced pressure source 112 to determine a source pressure generated by the reduced pressure source 112. The sensor may communicate with a processing unit (not shown) that monitors and controls the reduced pressure that is delivered by the reduced pressure source 112. The canister 110 may be a fluid reservoir, or collection member, to filter or hold exudates and other fluids removed from the tissue site 102. In one embodiment, the canister 110 and the reduced pressure source 112 are integrated into a single housing structure.

The fluid supply 116 may be used to deliver growth and/or healing agents to the scaffold 114 for the incisional wound 104 including, without limitation, an antibacterial agent, an antiviral agent, a cell-growth promotion agent, an irrigation fluid, or other chemically active agents. The system 100 further comprises a first valve 127 positioned in the third conduit 117 to control the flow of fluid 118 to the scaffold 114, and a second valve 123 positioned in the second conduit 113 between the reduced pressure source 112 and the juncture between the second conduit 113 and the third conduit 117 to control the flow of reduced pressure. The processing unit of the reduced pressure treatment unit 120 is operatively connected to the first and second valves 127, 123 to control the delivery of reduced pressure and/or fluid from the fluid supply 116, respectively, to the scaffold 114 as required by the particular therapy being administered to the patient. The fluid supply 116 may deliver the fluids as indicated above, but may also deliver air to the scaffold 114 to promote healing and facilitate drainage of the incisional wound 104. The fluid 118 may be gas or liquid, and may contain growth factors, healing factors, or other substances to treat the incisional wound 104 at the tissue site 102. For example, the fluid 118 may be water, saline, or dye saline.

The term "scaffold" as used herein refers to a substance or structure applied to or positioned in a wound or defect that provides a structural matrix for the growth of cells and/or the formation of tissue. A scaffold is a three-dimensional, porous structure having dimensions roughly corresponding to the shape of the specific wound defect. The scaffold 114 may be infused with, coated with, or comprised of cells, growth factors, extracellular matrix components, nutrients, proteins, or other substances to promote cell growth. The scaffold 114 may possess characteristics of a manifold by directing the flow of fluids through its structural matrix. For example, the scaffold 114 may take on the characteristics of a manifold by directing reduced pressure or delivering fluids to a tissue site, or removing fluids from a tissue site. As used herein, the term "manifold" refers to a substance or structure that is provided to assist in directing reduced pressure or delivering fluids to a tissue site, or removing fluids from a tissue site. A manifold can include a plurality of flow channels or pathways that are interconnected to improve distribution of fluids provided to and removed from the area of tissue around the manifold. Examples of manifolds may include, without limitation, devices that have structural elements arranged to form flow channels, cellular foams such as open-cell foam, porous tissue collections, and liquids, gels and foams that include or cure to include flow channels. The scaffold 114 possesses the characteristics of a manifold as described above.

The scaffold 114 may be a biologic or synthetic scaffold used to support protein adhesion and cellular in-growth for tissue repair and regeneration. The current state of the art in scaffold technology relies upon the inherent characteristics of the surrounding tissue space for the adsorption of proteins and migration of cells. The scaffold 114 for use according to the invention, and coupled with its function as a manifold, provides physical guidance to direct the pathway of fluid flow within the incisional wound 104, creating avenues for the movement and migration of adhesive proteins and cells, respectively, which are integral to the establishment of a provisional matrix in predetermined patterns of organization within the tissue space. The methods and apparatuses described for fluid flow-induced generation of tissues have direct implications into the design of the scaffold 114. In certain aspects, the scaffold 114 may be a reticulated structure, such as, for example, a reticulated foam, comprising a high void fraction for improved bioabsorption properties.

Non-limiting examples of suitable scaffold materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyethylene glycols, poloxamers, polyphosphazenes, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold 114 can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold 114 comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold 114 may comprise combinations of any two, three or more materials, either in separate areas of the scaffold 114 or combined non-covalently, or covalently (e.g., copolymers such as a polyethylene oxide-polypropylene glycol block copolymers, or terpolymers), or combinations thereof.

In one embodiment, the scaffold 114 is formed from a scaffold material comprising PLGA fibers formed by a felting process that also functions as a manifold as described above. Such material known as Scaftex™ is available from Biomedical Structures, Inc. Any of the biodegradable or bioresorbable materials listed above that are reticulated and possess a high void fraction (low mass for degradation or resorption) may be used. The elastomeric materials, pliable materials, and gels are embodiments that are preferred for soft-tissue applications such as the incisional wound 104. The scaffold 114 is relatively thin between the opposing, interfacial surfaces 145, 147 which are positioned adjacent the incisional walls 109, 108, respectively, of the incisional wound 104. In one non-limiting example, the scaffold 114 may be approximately 0.25 mm to 3.0 mm thick between the opposing, interfacial surfaces 145, 147. Comparing the thickness of the scaffold 114 to the length and depth of the incisional wound 104, the scaffold 114 may be described as being relatively thin. In one embodiment, a ratio of the length to the thickness of the scaffold 114 is greater than about 10. Preferably, the scaffold 114 should be as thin as possible to fit within the incisional wound 104, minimizing the distance between the incisional walls 108, 109 to facilitate tissue apposition. Although the scaffold 114 is sufficiently thin, the material forming the scaffold 114 still comprises a matrix of pathways (not shown) to facilitate the flow of fluid between the incisional walls 108, 109. These pathways of the scaffold 114 extend through the scaffold 114 between the opposing, interfacial surfaces 145, 147 to induce tissue apposition by promoting the growth of tissue between the incisional walls 108, 109 as an interfacial scaffold matrix within the incisional wound 104.

The scaffold 114 may be of any size or shape depending on a variety of factors such as, for example, the type and size of the incisional wound 104 and the type of treatment being implemented to repair the wound. For example, the scaffold 114 may be substantially rectangular extending the full length of the incisional wound 104 along the longitudinal axis and the full depth of the incisional walls 108, 109 along the transverse axis. The scaffold 114 of such dimensions forms a full interfacial scaffold matrix between the two incisional walls 108, 109 to induce tissue apposition between the two. However, depending on the treatment, the scaffold 114 may only partially contact the incisional walls 108, 109. For example, the scaffold 114 may not extend to the bottom of the incisional wound 104 into the subcutaneous tissues 107. The upper edge portion 124 of the scaffold 114 may be positioned flush with the incisional opening 103 of the incisional wound 104 adjacent the epidermis 105, and secured within the incisional wound 104 by a plurality of sutures 130 that close the incisional wound 104 when stitched.

The scaffold 114 may further comprise an internal manifold structure 140 to supplement the flow of fluid through the reticulated pathways that already exist within the scaffold 114. The internal manifold structure 140 may comprise one or a plurality of primary flow channels 141 fluidly coupled to the conduit connector 115 that extend generally longitudinally through the scaffold 114 between the incisional walls 108, 109. The internal manifold structure 140 may also comprise additional tributary channels 143 fluidly coupled to one or more of the primary flow channels 141. The tributary channels 143 extend generally transversely within the scaffold 114 between the opposing, interfacial surfaces 145, 147 to further facilitate fluid flow over a larger area of the interfacial scaffold matrix within the incisional wound 104. The tributary channels 143 may extend from the primary flow channel 141 in any direction relative to the primary flow channel 141 and may form any shape to enhance the area of the scaffold 114 covering the interfacial surfaces 145, 147. For example, as shown in a specific, non-limiting embodiment, the tributary channels 143 extend in a direction generally perpendicular from the primary flow channel 141 in a linear direction as opposed to having a curved shape. Thus, the internal manifold structure 140 provides a supplemental matrix for fluid flow coextensive with the reticulated pathways of the scaffold 114 by using the plurality of primary flow channels 141 or a single primary channel that may include the plurality of tributary channels 143 or a combination of both. This supplemental matrix of the internal manifold structure 140 may be formed with a pattern that further induces apposition of the incisional walls 108, 109.

Although the primary flow channel 141 is shown as a generally tubular shape in the figures, the primary flow channel 141 may be a variety of different shapes as long as such flow channel extends generally longitudinally through the scaffold 114 between the incisional walls 108, 109. The primary flow channel 141 does not need to be straight, but may undulate longitudinally within the scaffold 114 between the upper edge portion 124 and lower edge portion 125. The primary flow channel 141 may also be an anisotropic material property of the scaffold 114 itself extending generally longitudinally between the incisional walls 108, 109. For example, the anisotropic property may be a differential resistance to fluid flow through interconnected pores within the scaffold 114 extending along a generally longitudinal axis of the scaffold 114. The anisotropic property may also be the alignment of pores and their interconnectivity within the scaffold 114, or the variation of pore size within the scaffold 114 that permits or facilitates fluid flow along a longitudinal axis of the scaffold 114. In another embodiment, the primary flow channel 141 may be formed by a bioresorbable tubing.

The tributary channels 143 may be asymmetric in shape and formed from anisotropic properties of the scaffold 114. In another embodiment, the tributary channels 143 may be formed by a bioresorbable tubing. Although inlets of the tributary channels 143 are shown extending from the surface of the primary flow channel 141, the tributary channels 143 may also extend from loci within the primary flow channel 141 and diverge within the scaffold 114 as non-parallel, asymmetric passages. The inlets of such tributary channels 143 are in fluid communication with the primary flow channel 141 to facilitate the flow of fluids between the incisional walls 108, 109. The inlets of several tributary channels 143 may also originate and diverge from a single locus within the primary flow channel 141 in a star-pattern, for example, generally in parallel with and between the incisional walls 108, 109.

Figure 3:
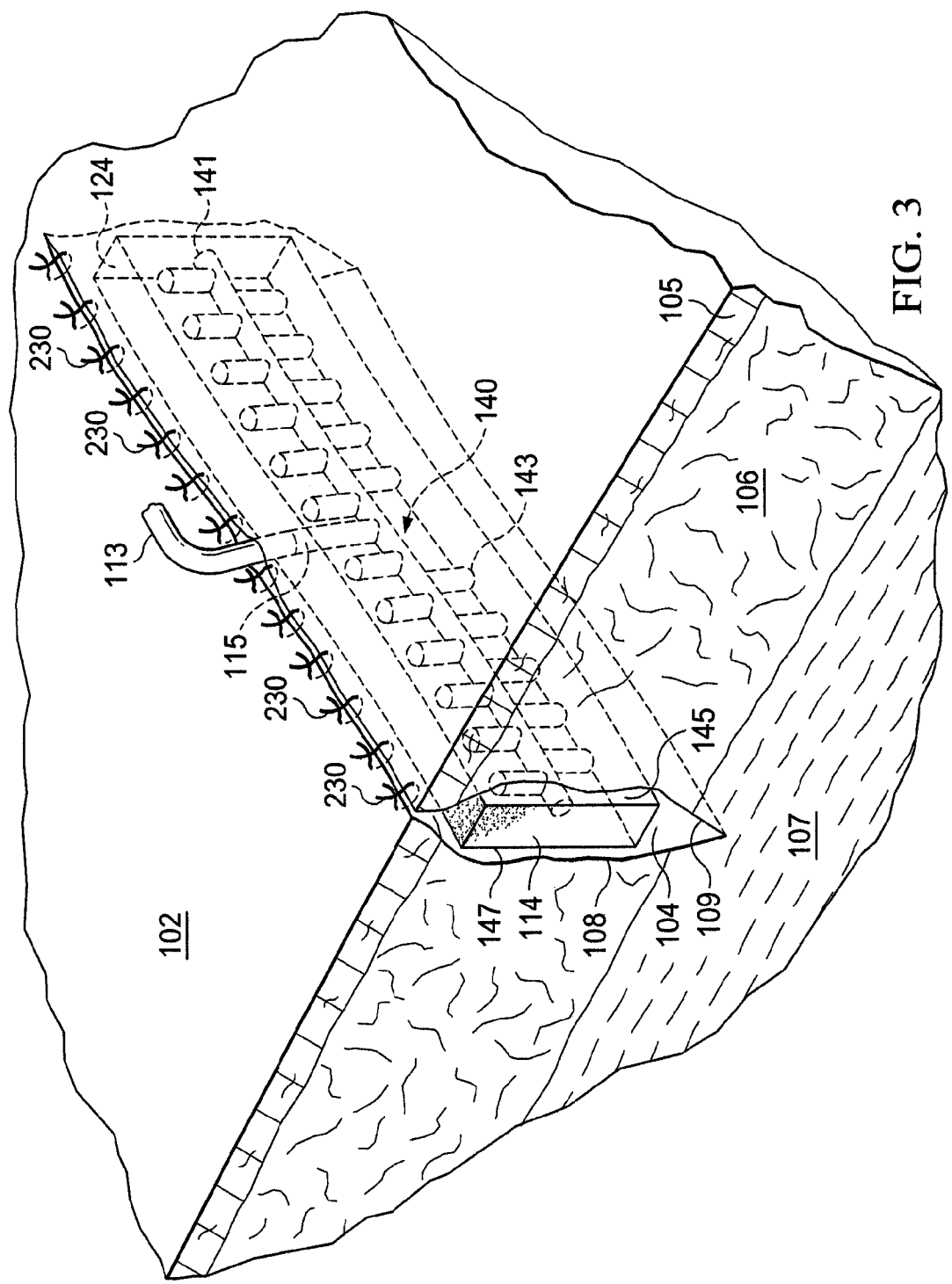
FIG. 3 is a schematic, cross-sectional, perspective view of an incisional wound and the scaffold shown in FIG. 1 positioned below the opening of the incisional wound.

Referring to FIG. 3, the scaffold 114 may be positioned within the incisional wound 104 so that the upper edge portion 124 of the scaffold 114 is seated below the epidermis 105 such that sutures 230 may be used to close the entire scaffold 114 within the incisional wound 104. Seating the upper edge portion 124 of the scaffold 114 below the epidermis 105 of the incisional wound 104 may facilitate closure of the incisional opening 103 of the incisional wound 104 and help maintain the reduced-pressure within the incisional wound 104 for a longer period of time. Referring back to FIG. 2, in an alternative embodiment (not shown) the upper edge portion 124 of the scaffold 114 may protrude out of the incisional opening 103 above the epidermis 105 so that the sutures 130 may be stitched through the upper portion of the scaffold 114 to hold it firmly in place within the incisional wound 104. In this embodiment, the sutures 130 may be stitched sufficiently tight to substantially close the incisional opening 103 of the wound to further facilitate healing as described above.

Figure 4:
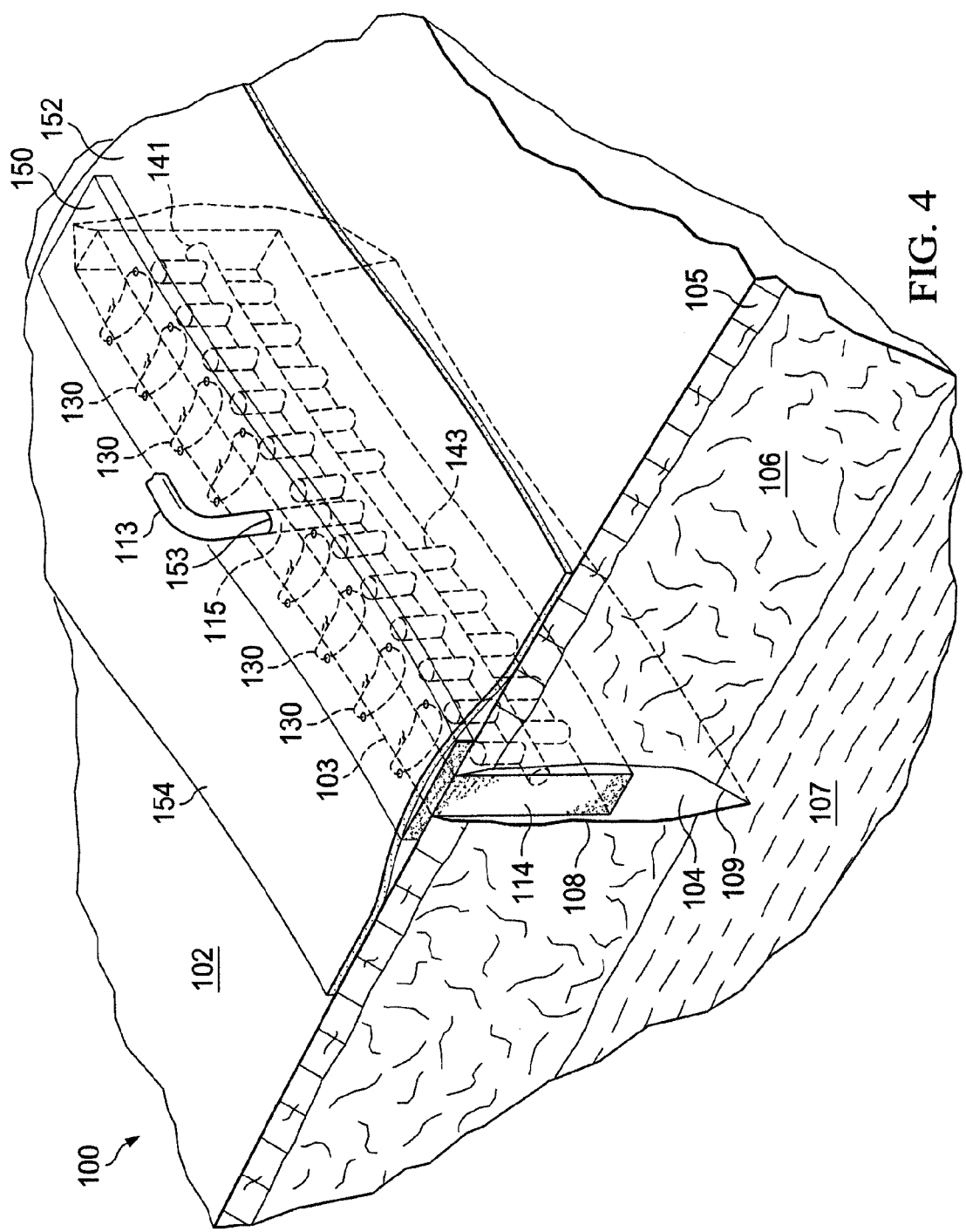
FIG. 4 is a schematic, cross-sectional, perspective view of an incisional wound and the scaffold shown in FIG. 2 including a drape covering the incisional wound.

In another embodiment shown in FIG. 4, the scaffold 114 may be exposed through the incisional opening 103 in the epidermis 105 as opposed to being closed within the incisional wound 104. In this embodiment, the system 100 may further comprise an external manifold 150 in fluid communication with the scaffold 114 and a drape 152 covering the external manifold 150 to maintain reduced pressure beneath the drape 152 within the incisional wound 104. The drape 152 includes an aperture 153 through which the conduit connector 115 extends to provide fluid communication between the second conduit 113 and the external manifold 150. The drape 152 may also include a periphery portion 154 that extends beyond the incisional opening 103 and includes an adhesive or bonding agent (not shown) to secure the drape 152 to the healthy tissue adjacent the incisional opening 103. The adhesive provides a seal between the drape 152 and the epidermis 105 to better maintain reduced pressure within the incisional wound 104. In another embodiment, a seal layer (not shown) such as, for example, a hydrogel or other material, may be disposed between the drape 152 and the epidermis 105 to augment or substitute for the sealing properties of the adhesive. The drape 152 may also be used in conjunction with the embodiments shown in FIGS. 2 and 3 described above.

The drape 152 may be any material that provides a pneumatic or fluid seal. The drape 152 may, for example, be an impermeable or semi-permeable, elastomeric material. As stated above, the drape 152 may include an adhesive layer on the periphery portion 154.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

It will be understood that the benefits and advantages described above may relate to one embodiment or may relate to several embodiments. It will further be understood that reference to "an" item refers to one or more of those items.

Where appropriate, aspects of any of the examples and embodiments described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

We claim:

1. A method for treating an incisional wound having incisional walls, the method comprising:
   fluidly coupling a conduit to a source of reduced pressure, the conduit having a first end for receiving reduced pressure and a second end;
   fluidly coupling a scaffold to the second end of said conduit for receiving the reduced pressure, wherein the scaffold is formed from sufficiently thin porous material having an internal manifold extending generally longitudinally between opposing surfaces of the scaffold, the internal manifold having a primary flow channel comprised of bioresorbable tubing;

positioning the opposing surfaces of the scaffold between the incisional walls of the incisional wound;

fluidly coupling the internal manifold to the second end of the conduit for receiving the reduced pressure;

surgically closing the incisional wound to maintain the reduced pressure therein; and providing the reduced pressure through the conduit to the scaffold and the internal manifold for the incisional wound, whereby the scaffold induces tissue apposition between the incisional walls.

2. The method of claim 1, wherein said scaffold includes an edge portion adjacent the opposing surfaces, the method further comprising:

adjusting said scaffold between the incisional walls so the edge portion is not in contact with the incisional walls;

positioning an external manifold in fluid communication with the edge portion; and placing a drape formed of substantially impermeable material over said external manifold and said scaffold.

3. The method of claim 2, further comprising positioning the external manifold outside the incisional wound.

4. The method of claim 1, wherein the scaffold includes an edge portion adjacent the opposing surfaces, and wherein the incisional wound has an opening between the incisional walls, the method further comprising:

positioning said edge portion below the opening and in contact with the incisional walls; and covering the surgically closed incisional wound with a substantially impermeable material to substantially maintain the reduced pressure within the incisional wound.

5. A method for treating an incisional wound having incisional walls, the method comprising:

positioning opposing surfaces of a scaffold between the incisional walls of the incisional wound, the scaffold having a thickness between the opposing surfaces that is sufficiently thin for positioning within the incisional wound;

fluidly coupling a source of reduced pressure to an internal manifold having a primary flow channel extending generally longitudinally within the scaffold and between the opposing surfaces, the primary flow channel being formed of bioresorbable tubing;

providing reduced pressure from the source of reduced pressure to the incisional wound through the internal manifold and the scaffold; and inducing tissue apposition between the incisional walls as the reduced pressure is provided to the incisional wound.

6. The method of claim 5, further comprising closing the incisional wound to maintain the reduced pressure within the incisional wound.

7. The method of claim 5, wherein the scaffold includes an edge portion adjacent the opposing surfaces, the method further comprising:

adjusting the scaffold between the incisional walls so the edge portion is removed from the incisional walls;

positioning an external manifold in fluid communication with the edge portion; and covering the external manifold and the scaffold with a drape formed of a substantially impermeable material.

8. The method of claim 7, further comprising positioning the external manifold outside the incisional wound.

9. The method of claim 5, wherein the scaffold includes an edge portion adjacent the opposing surfaces, and wherein the incisional wound has an opening between the incisional walls, the method further comprising:

positioning the edge portion below the opening and in contact with the incisional walls; and covering the incisional wound with a substantially impermeable material to substantially maintain the reduced pressure within the incisional wound.

10. The method of claim 5, wherein the scaffold is formed from porous material.

11. The method of claim 5, wherein the scaffold is generally elongated in shape.

12. The method of claim 5, wherein the opposing surfaces of the scaffold are positioned in direct contact with the incisional walls.

13. The method of claim 5, wherein the opposing surfaces of the scaffold are positioned adjacent the incisional walls.

14. The method of claim 5, wherein the scaffold has a length and a width, and wherein the thickness of the scaffold is less than the length and the width.

15. The method of claim 5, further comprising fluidly coupling a conduit in fluid communication between the source of reduced pressure and the internal manifold.

16. The method of claim 5, wherein the internal manifold further comprises tributary flow channels fluidly coupled to the primary flow channel and extending generally transversely within the scaffold between the opposing surfaces.

* * * * *